United States Patent
Walther et al.

(10) Patent No.: US 10,526,562 B2
(45) Date of Patent: Jan. 7, 2020

(54) COMPOSITION HAVING A MUGUET ODOR

(71) Applicant: FIRMENICH SA, Geneva (CH)

(72) Inventors: Eric Walther, Geneva (CH); Julien Coulomb, Geneva (CH)

(73) Assignee: Firmenich SA, Geneva (CH)

(*) Notice: Subject to any disclaimer, the term of this patent is extended or adjusted under 35 U.S.C. 154(b) by 0 days.

(21) Appl. No.: 16/342,089

(22) PCT Filed: Jan. 17, 2018

(86) PCT No.: PCT/EP2018/051057
§ 371 (c)(1),
(2) Date: Apr. 15, 2019

(87) PCT Pub. No.: WO2018/134220
PCT Pub. Date: Jul. 26, 2018

(65) Prior Publication Data
US 2019/0249111 A1    Aug. 15, 2019

(30) Foreign Application Priority Data
Jan. 18, 2017   (EP) ..................................... 17151937

(51) Int. Cl.
*C11B 9/00* (2006.01)
*C07C 45/45* (2006.01)
*C07C 47/27* (2006.01)

(52) U.S. Cl.
CPC ............ *C11B 9/0061* (2013.01); *C07C 45/45* (2013.01); *C07C 47/27* (2013.01)

(58) Field of Classification Search
CPC ............................... C11B 9/0061; C07C 47/27
See application file for complete search history.

(56) References Cited

U.S. PATENT DOCUMENTS

| | | | |
|---|---|---|---|
| 4,396,670 A | 8/1983 | Sinclair | |
| 4,491,537 A * | 1/1985 | Fujioka | C07C 45/49 424/69 |
| 2016/0075627 A1* | 3/2016 | Goeke | C07C 47/228 435/188 |
| 2016/0369205 A1* | 12/2016 | Goeke | C07C 47/228 |

FOREIGN PATENT DOCUMENTS

| | | |
|---|---|---|
| EP | 0 368 156 A1 | 5/1990 |
| WO | 01/41915 A1 | 6/2001 |
| WO | 2014/180945 A1 | 11/2014 |
| WO | 2014/180952 A1 | 11/2014 |
| WO | 2014/207205 A1 | 12/2014 |

OTHER PUBLICATIONS

International Search Report and Written Opinion, Appl. No. PCT/EP2018/051057, dated Mar. 14, 2018.
Bonatz et al., "Amino resin microcapsules. III. Release properties," Acta Polymerica, 40(11): 683-690, dated Nov. 1989.
Bône et al., "Microencapsulated Fragrances in Melamine Formaldehyde Resins," CHIMIA, 65(3): 177-181, dated Mar. 2011.
Dietrich et al., "Amino resin microcapsules. I. Literature and patent review," Acta Polymerica, 40(4): 243-251, dated Apr. 1989.
Dietrich et al., "Amino resins microcapsules. II. Preparation and morphology," Acta Polymerica, 40(5): 325-331, dated May 1989.
Dietrich et al., "Amino resin microcapsules. IV. Surface tension of the resins and mechanism of capsule formation," Acta Polymerica, 41(2): 91-95, dated Feb. 1990.
Herrmann, "Controlled Release of Volatiles under Mild Reaction Conditions: From Nature to Everyday Products," Angew. Chem. Int. Ed., 46 (31):5836-5863, dated Oct. 2007.
Lee et al., "Microencapsulation of fragrant oil via in situ polymerization: effects of pH and melamine-formaldehyde molar ratio," J. Microencapsulation, 19(5): 559-569, dated Sep. 2002.
Ma et al., "Copolymerization of Isobutene with 4-(2-Hydroxyl-2-methylpropyl) Styrene Co-initiated by TiCl4 in the Presence of ED," Journal of Macromolecular Science, Part A, 40(4):345-356, Jan. 4, 2003.

* cited by examiner

*Primary Examiner* — Arrie L Reuther
(74) *Attorney, Agent, or Firm* — Armstrong Teasdale LLP

(57) ABSTRACT

A composition of matter including:
a) at least one compound of formula (I)

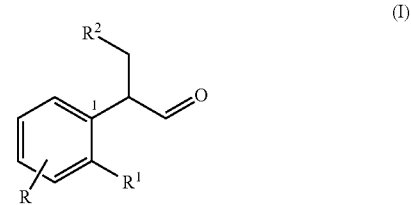

(I)

in the form of any one of its isomers or a mixture thereof; wherein $R^1$ represents a hydrogen atom or a $C_{1-2}$ alkyl group; $R^2$ represents a hydrogen atom or a methyl group; and R represents a group of formula —$[CH_2]_n$ $C(Me)_2OH$, wherein n is 0, 1 or 2; with R being, relative to position 1, an ortho, meta or para substituent of the aromatic ring; and
b) at least one compound of formula

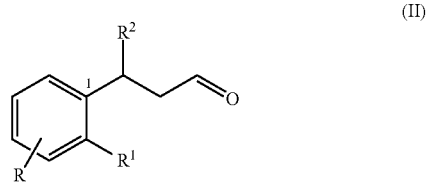

(II)

in the form of any one of its isomers or a mixture thereof; wherein $R^1$, $R^2$ and R have the same meaning as defined in formula (I);
uses of the composition of matter as perfuming ingredients, perfuming compositions and in consumer products, along with a process to prepare the composition of matter.

17 Claims, No Drawings

COMPOSITION HAVING A MUGUET ODOR

This application is a 371 filing of International Patent Application PCT/EP2018/051057 filed Jan. 17, 2018, which claims the benefit of European application no. 17151937.4 filed Jan. 18, 2017.

TECHNICAL FIELD

The present invention relates to the field of perfumery. More particularly, it relates to a composition of matter comprising at least one compound of formula (I) and at least one compound (II) as perfuming ingredients as well as the composition and the consumer product including such composition of matter. The process to obtain the invention's composition of matter is also part of the present invention.

BACKGROUND

One of the key ingredients in the perfumery industry is Lyral® (4/3-(4-hydroxy-4-methylpentyl)-3-cyclohexene-1-carbaldehyde; origin International Flavors & Fragrances, USA). However the use of said ingredient, appreciated for this floral, lily of the valley, hydroxycitronellal odor note which is different from the note imparted by Lilial® (2-methyl-3-[4-(2-methyl-2-propanyl)phenyl]propanal, trademark from Givaudan-Roure SA, Vernier, Suisse), has been restricted as it is listed as an allergen.

So, there is a need to develop novel perfuming ingredients which could be used as Lyral® replacers.

The present invention provides a composition of matter comprising at least one compound of formula (I) and at least one compound of formula (II) having characteristic odors very close to Lyral®.

To the best of our knowledge, only one closely related structural analogue of compound of formula (I) and of compound of formula (II) has been reported in the literature as perfuming ingredient. Actually, 3-(4-(2-hydroxypropan-2-yl)phenyl)butanal has been reported in U.S. Pat. No. 4,491,537 as having a green, woody, peach like aroma, i.e. a totally different organoleptic profile from the present invention's compounds.

Another analogue, 3-(3-(3-hydroxy-3-methylbutyl)phenyl)-2-methylpropanal, has been disclosed in WO 2014207205 without specifying its organoleptic properties. Said compound has been used as an intermediate towards the perfuming ingredient 2-methyl-3-(3-(3-methylbut-3-en-1-yl)phenyl)propanal.

Both prior art documents do not report or suggest any organoleptic properties of the composition of matter comprising compounds of formula (I) and compound of formula (II), or any use of said compounds in the field of perfumery.

SUMMARY OF THE INVENTION

The invention relates to a composition of matter comprising at least one compound of formula (I) and at least one compound of formula (II) which could be used as a Lyral® replacer.

So, a first object of the present invention is a composition of matter comprising:
a) at least one compound of formula

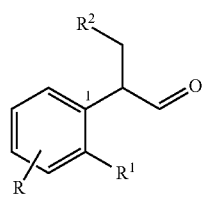

(I)

in the form of any one of its isomers or a mixture thereof; wherein $R^1$ represents a hydrogen atom or a $C_{1-2}$ alkyl group; $R^2$ represents a hydrogen atom or a methyl group; and R represents a group of formula —$[CH_2]_nC(Me)_2OH$, wherein n is 1 or 2; said R being, relative to position 1, an ortho, a meta, a para substituent of the aromatic ring or a mixture thereof; and b) at least one compound of formula

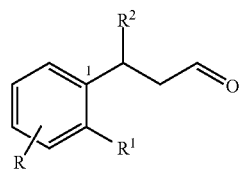

(II)

in the form of any one of its isomers or a mixture thereof; wherein $R^1$, $R^2$ and R have the same meaning as defined in formula (I); said R being, relative to position 1, an ortho, a meta, a para substituent of the aromatic ring or a mixture thereof.

A second object of the present invention is the use as perfuming ingredient of a composition of matter, comprising compound of formula (I) and compound of formula (II), as defined above.

A third object of the present invention is a perfuming composition comprising
i) at least a composition of matter, comprising compound of formula (I) and compound of formula (II), as defined above;
ii) at least one ingredient selected from the group consisting of a perfumery carrier and a perfumery base; and
iii) optionally at least one perfumery adjuvant.

Another object of the present invention is a perfumed consumer product comprising at least a composition of matter, comprising compound of formula (I) and compound of formula (II), as defined above or a perfuming composition as defined above.

Another object of the present invention is a process to prepare the composition of matter as defined above comprising the step of reacting allyl alcohol or crotyl alcohol with compound of formula

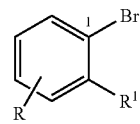

(V)

wherein R and $R^1$ have the same meaning as defined above; said R being, relative to position 1, an ortho, a meta, a para substituent of the aromatic ring or a mixture thereof; under Heck coupling conditions.

A last object of the present invention is a method to confer, enhance, improve or modify the odor properties of a perfuming composition or of a perfumed article, which method comprises adding to said composition or article an effective amount of at least a composition of matter as defined above.

DESCRIPTION OF THE INVENTION

Unless stated otherwise, percentages (%) are meant to designate percent by weight relative to the total weight of the composition.

Surprisingly, it has now been discovered that a composition of matter, comprising at least one compound of formula (I) and at least one compound of formula (II), exhibits a very interesting odor note with a lily of the valley twist in the direction of Lyral® which is particularly appreciated. This composition of matter has also never been disclosed.

A first object of the present invention is a composition of matter comprising a) at least one compound of formula

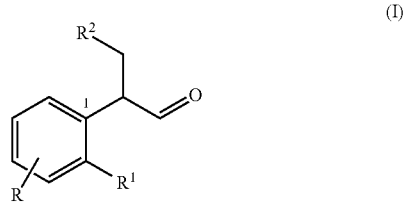

in the form of any one of its isomers or a mixture thereof; wherein $R^1$ represents a hydrogen atom or a $C_{1-2}$ alkyl group; $R^2$ represents a hydrogen atom or a methyl group; and R represents a group of formula —$[CH_2]_nC(Me)_2OH$, wherein n is 1 or 2; said R being, relative to position 1, an ortho, a meta, a para substituent of the aromatic ring or a mixture thereof; and b) at least one compound of formula

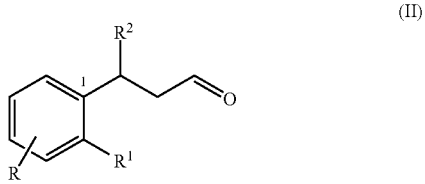

in the form of any one of its isomers or a mixture thereof; wherein $R^1$, $R^2$ and R have the same meaning as defined in formula (I); said R being, relative to position 1, an ortho, a meta, a para substituent of the aromatic ring or a mixture thereof. Said composition of matter can be used as perfuming ingredient, for instance to impart odor notes of the lily of the valley type in the direction of Lyral®.

For the sake of clarity, by the expression "$R^1$, $R^2$ and R have the same meaning as in formula (I)", or similar, it is meant the normal meaning understood by a person skilled in the art, i.e. that the invention's composition of matter comprises compounds of formula (I) and (II) wherein $R^1$ group of compound of formula (I) is identical to $R^1$ group of compound of formula (II), $R^2$ group of compound of formula (I) is identical to $R^2$ group of compound of formula (II) and R group of compound of formula (I) is identical to R group of compound of formula (II). In other words, the substituents of the compound of formula (I) are identical to the substituents of the compound of formula (II).

For the sake of clarity, by the expression "composition of matter", or similar, it is meant the normal meaning understood by a person skilled in the art, i.e. that at least two different compounds (which are not stereoisomers) are present. According to any one of the above embodiments, the invention's composition of matter may comprise at least one compound of formula (I) in an amount comprised between 0.5% w/w and 60% w/w and at least 40% w/w of at least one compound of formula (II), relative to the total weight of the composition of matter. Preferably, the invention's composition of matter may comprise compound of formula (I) in an amount comprised between 0.5% w/w and 49% w/w and at least 50% w/w of compound of formula (II), relative to the total weight of the composition of matter. Preferably, the invention's composition of matter may comprise compound of formula (I) in an amount comprised between 1% w/w and 30% w/w and at least 70% w/w of compound of formula (II), relative to the total weight of the composition of matter. Even, more preferably, the invention's composition of matter may comprise compound of formula (I) in an amount comprised between 1% w/w and 15% w/w and at least 85% w/w of compound of formula (II), relative to the total weight of the composition of matter.

For the sake of clarity, by the expression "any one of" its isomers or a mixture thereof, or similar, it is meant the normal meaning understood by a person skilled in the art, i.e. that the invention's compound can be a pure enantiomer (if chiral), a mixture of enantiomers (mixture of stereoisomers), a pure regioisomer, a mixture of regioisomers or a mixture thereof.

For the sake of clarity, by the expression "a pure regioisomer or a mixture of regioisomers", or similar, it is meant the normal meaning understood by a person skilled in the art, i.e. that the R group of compound (I) may be, relative to position 1, a ortho, a meta, a para substituent or a mixture thereof and the R group of compound (II) may be, relative to position 1, an ortho, a meta, a para substituent or a mixture thereof. For example, the invention's composition of matter can comprise compounds being pure regioisomers, e.g. R being a para substituent of the aromatic ring, relative to position 1; or a mixtures of, for example, two regioisomers comprising compounds wherein R is a para substituent of the aromatic ring, relative to position 1 and compounds wherein R is a meta substituent of the aromatic ring, relative to position 1. In other words, the compound of formula (I) may be of formula (I') (i.e. R being an ortho substituent of the aromatic ring, relative to position 1), of formula (I'') (i.e. R being a meta substituent of the aromatic ring, relative to position 1) or of formula (I''') (i.e. R being a para substituent of the aromatic ring, relative to position 1) or a mixture thereof and compound of formula (II) may be of formula (II') (i.e. R being an ortho substituent of the aromatic ring, relative to position 1), of formula (II'') (i.e. R being a meta substituent of the aromatic ring, relative to position 1), of formula (II''') (i.e. R being a para substituent of the aromatic ring, relative to position 1) or a mixture thereof. Each compound of formula (I'), (I'') or (I''') represents one regioisomer of the compound of formula (I) and each compound of formula (II'), (II'') or (II''') represents one regioisomer of the compound of formula (II). The compounds of formula (I') and (II') may also be called the ortho regioisomers. The compounds of formula (I'') and (II'') may also be called the meta regioisomers. And the compounds of formula (I''') and (II''') may also be called the para regioisomers.

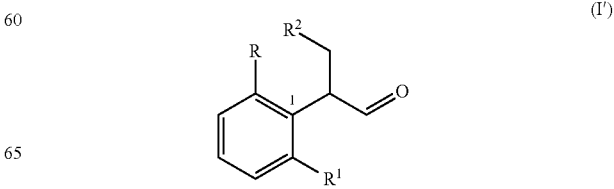

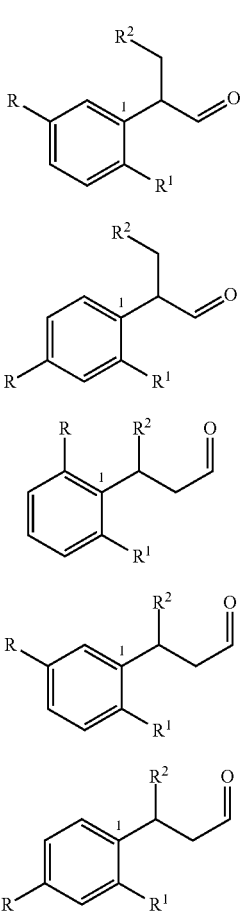

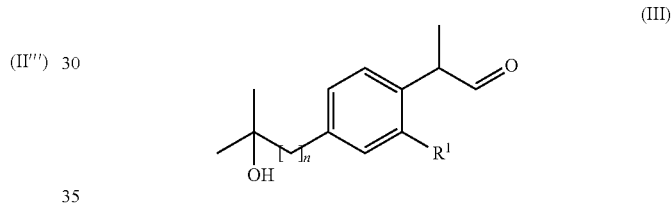

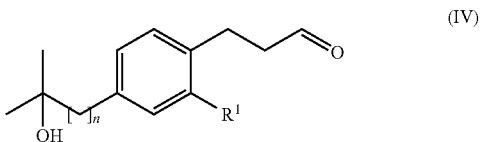

According to any one of the above embodiments, the invention's composition of matter comprises at least one compound of formula (I) having a R group being a para and/or a meta substituent relative to position 1 and at least one compound of formula (II) having a R group being a para and/or a meta substituent relative to position 1. Preferably, the invention's composition of matter comprises at least one compound of formula (I) and at least one compound of formula (II) being the same regioisomer, e.g. the composition of matter comprises at least the para regioisomer of formula (I) (compound of formula (I''')) and at least the para regioisomer of formula (II) (a compound of (II''')).

According to any one of the above embodiments, the invention's composition of matter comprises less than 5% w/w of the meta regioisomers; i.e. of compound of formula (II'') and of compound of formula (I''). Preferably, the invention's composition of matter comprises less than 2% w/w of the meta regioisomers; i.e. of compound of formula (II'') and of compound of formula (I'').

According to any one of the above embodiments, the invention's composition of matter comprises
at most 20% w/w of the compound of formula (I');
at most 20% w/w of the compound of formula (II');
at most 45% w/w of the compound of formula (II'');
at most 25% w/w of the compound of formula (I'');
from 25 to 99% w/w of the compound of formula (II''');
from 0.5 to 49% w/w of the compound of formula (I''');
wherein the percentages are expressed in a weight to weight basis relative to the total weight of said composition of matter.

Even more preferably, said mixture comprises
from 50 to 99% w/w of the compound of formula (II''');
from 1 to 49% w/w of the compound of formula (I''').

According to any one of the above embodiments, the invention's composition of matter may comprise only one regioisomer of formula (I) and only one regioisomer of formula (II) wherein the regioisomer of formula (I) is the same regioisomer of formula (II); i.e. a composition comprising compounds wherein the R group is an ortho substituent relative to position 1 (composition comprising compound of formula (I') and (II')), or a composition comprising compounds wherein the R group is a meta substituent, relative to position 1 (composition comprising compound of formula (I'') and (II'')) or a composition comprising compounds wherein the R group is an para substituent relative to position 1 (composition comprising compound of formula (I''') and (II''')). Preferably, the invention's composition of matter comprises compounds wherein the R group is a meta or para substituent relative to position 1. Even more preferably, the invention's composition of matter comprises compounds wherein the R group is a para substituent relative to position 1.

According to any one of the embodiments of the invention, said compound (I) is a compound of formula in the form of any one of its stereoisomers or a mixture thereof, and wherein n and $R^1$ have the same meaning as defined above.

According to any one of the embodiments of the invention, said compound (II) is a compound of formula wherein n and $R^1$ have the same meaning as defined above.

According to any one of the embodiments of the invention, said compound of formula (I) or (II) is a $C_{12}$-$C_{17}$, or even a $C_{13}$-$C_{14}$, compound.

According to any one of the embodiments of the invention, said invention's composition of matter comprises compounds wherein n is 1 or 2; preferably n is 1.

According to any one of the embodiments of the invention, said invention's composition of matter comprises compounds wherein $R^1$ represents a hydrogen atom or a $C_{1-2}$ alkyl group. Preferably $R^1$ represents a hydrogen atom or a methyl group. Most preferably, $R^1$ represents a hydrogen atom.

According to any one of the embodiments of the invention, said invention's composition of matter comprises compounds wherein $R^2$ represents a hydrogen atom or a methyl group. Preferably $R^2$ represents a hydrogen atom.

According to any one of the embodiments of the invention, said invention's composition of matter comprises compounds wherein n is 1 when $R^2$ represents a methyl group and n is 2 when $R^2$ represents hydrogen atom or a methyl group.

To the best of our knowledge, the composition of matter as herein above reported are novel, and therefore also an object of the present invention.

According to any one of the above embodiments of the invention, the invention's composition of matter comprises 3-[4-(2-hydroxy-2-methylpropyl)phenyl]propanal and 2-[4-(2-hydroxy-2-methylpropyl)phenyl]propanal. In particular, one may cite a composition of matter comprising 3-[4-(2-hydroxy-2-methylpropyl)phenyl]propanal in an amount comprised between 50% w/w and 99% w/w and 2-[4-(2-hydroxy-2-methylpropyl)phenyl]propanal in an amount comprised between 0.5% w/w and 49% w/w, relative to the weight of the composition of matter. As specific examples of the invention's composition of matter, one may cite, as non-limiting example, a composition comprising even consisting of about 86% w/w of 3-[4-(2-hydroxy-2-methylpropyl)phenyl]propanal and 14% w/w of 2-[4-(2-hydroxy-2-methylpropyl)phenyl]propanal, relative to the weight of the composition of matter. Said composition of matter is characterized by having an overall olfactive character very close to Lyral® (4/3-(4-hydroxy-4-methylpentyl)-3-cyclohexene-1-carbaldehyde; origin International Flavors & Fragrances, USA); i.e. the invention's composition of matter possesses a lily of the valley, hydroxycitronellal odor note allied with a "wet" effect very typical of Lyral®. The invention's composition of matter may be used to impart the odor of Lyral®. In other words, the invention's composition of matter may be employed as an olfactive substitutes for this ingredient which is highly sought by the the industry since Lyral® is now limited in use for allergenic reasons. In fact, when said composition of matter is compared with Lyral®, the invention's composition of matter distinguishes itself by being more substantive and powerful (thus allowing even lower level of dosage compared to the prior art compound) as well as having an improved radiance, while (to the contrary of many supposed substitute of Lyral®) delivering also the unique "wet" effect of Lyral®.

As mentioned above, the invention relates to the use of a composition of matter comprising at least one compound of formula (I) and at least one compound of formula (II) as a perfuming ingredient. In other words, it concerns a method to confer, enhance, improve or modify the odor properties of a perfuming composition or of a perfumed article, which method comprises adding to said composition or article an effective amount of at least the invention's composition of matter. By "use of a composition of matter" it has to be understood here also the use of any composition containing a composition of matter and which can be advantageously employed in the perfumery industry.

In particular, said method or use can be directed to a method to replace Lyral® in perfuming compositions. Or similarly to confer, enhance, improve or modify the floral, lily of the valley, hydroxycitronellal odor note of a perfuming composition or of a perfumed article.

Said composition of matter, which in fact can be advantageously employed as perfuming ingredient, is also an object of the present invention.

Therefore, another object of the present invention is a perfuming composition comprising:
i) as a perfuming ingredient, at least one invention's composition of matter as defined above;
ii) at least one ingredient selected from the group consisting of a perfumery carrier and a perfumery base; and
iii) optionally at least one perfumery adjuvant.

By "perfumery carrier", it is meant a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as butylene or propylene glycol, glycerol, dipropyleneglycol and its monoether, 1,2,3-propanetriyl triacetate, dimethyl glutarate, dimethyl adipate 1,3-diacetyloxypropan-2-yl acetate, diethyl phthalate, isopropyl myristate, benzyl benzoate, benzyl alcohol, 2-(2-ethoxyethoxy)-1-ethano, tri-ethyl citrate or mixtures thereof, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company), or hydrogenated castors oils such as those known under the trademark Cremophor® RH 40 (origin: BASF).

Solid carrier is meant to designate a material to which the perfuming composition or some element of the perfuming composition can be chemically or physically bound. In general such solid carriers are employed either to stabilize the composition, or to control the rate of evaporation of the compositions or of some ingredients. The use of solid carrier is of current use in the art and a person skilled in the art knows how to reach the desired effect. However by way of non-limiting example of solid carriers, one may cite absorbing gums or polymers or inorganic materials, such as porous polymers, cyclodextrines, wood based materials, organic or inorganic gels, clays, gypsum talc or zeolites.

As other non-limiting examples of solid carriers, one may cite encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs-und Geliermittel in Lebensmitteln, Band 2 der Schriftenreihe Lebensmittelchemie, Lebensmittelqualitat, Behr's Verlag GmbH & Co., Hamburg, 1996. The encapsulation is a well-known process to a person skilled in the art, and may be performed, for instance, by using techniques such as spray-drying, agglomeration or yet extrusion; or consists of a coating encapsulation, including coacervation and complex coacervation technique.

As non-limiting examples of solid carriers, one may cite in particular the core-shell capsules with resins of aminoplast, polyamide, polyester, polyurea or polyurethane type or a mixture thereof (all of said resins are well known to a person skilled in the art) using techniques like phase separation process induced by polymerization, interfacial polymerization, coacervation or altogether (all of said techniques have been described in the prior art), optionally in the presence of a polymeric stabilizer or of a cationic copolymer.

Resins may be produced by the polycondensation of an aldehyde (e.g. formaldehyde, 2,2-dimethoxyethanal, glyoxal, glyoxylic acid or glycolaldehyde and mixtures thereof) with an amine such as urea, benzoguanamine, glycoluryl, melamine, methylol melamine, methylated methylol melamine, guanazole and the like, as well as mixtures thereof. Alternatively one may use preformed resins alkylolated polyamines such as those commercially available under the trademark Urac® (origin: Cytec Technology Corp.), Cy Mel® (origin: Cytec Technology Corp.), Urecoll® or Luracoll® (origin: BASF).

Others resins are the ones produced by the polycondensation of a polyol, like glycerol, and a polyisocyanate, like a trimer of hexamethylene diisocyanate, a trimer of isophorone diisocyanate or xylylene diisocyanate or a Biuret of hexamethylene diisocyanate or a trimer of xylylene diisocyanate with trimethylolpropane (known with the tradename of Takenate®, origin: Mitsui Chemicals), among which a trimer of xylylene diisocyanate with trimethylolpropane and a Biuret of hexamethylene diisocyanate.

Some of the seminal literature related to the encapsulation of perfumes by polycondensation of amino resins, namely melamine based resins with aldehydes includes articles such as those published by K. Dietrich et al. in Acta Polymerica, 1989, vol. 40, pages 243, 325 and 683, as well as 1990, vol. 41, page 91. Such articles already describe the various parameters affecting the preparation of such core-shell microcapsules following prior art methods that are also further detailed and exemplified in the patent literature. U.S. Pat. No. 4,396,670, to the Wiggins Teape Group Limited is a pertinent early example of the latter. Since then, many other authors have enriched the literature in this field and it would be impossible to cover all published developments here, but the general knowledge in encapsulation technology is very significant. More recent publications of pertinence, which disclose suitable uses of such microcapsules, are represented for example by the article of H. Y. Lee et al. in Journal of Microencapsulation, 2002, vol. 19, pages 559-569, international patent publication WO 01/41915 or yet the article of S. Bóne et al. in Chimia, 2011, vol. 65, pages 177-181.

By "perfumery base" what is meant here is a composition comprising at least one perfuming co-ingredient.

Said perfuming co-ingredient is not of formula (I) and (II). Moreover, by "perfuming co-ingredient" it is meant here a compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to the intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or *sulphurous* heterocyclic compounds and essential oils, and said perfuming co-ingredients can be of natural or synthetic origin or even pro-perfumes (i.e. compounds which upon degradation liberate a perfuming ingredient). Examples of pro-perfumes have been described in the literature such as in the article published by A. Herrmann in Angewandte Chemie International Edition, 2007, vol. 46, p. 5836-5863 or in more recent work of similar type, as well as in the abundant patent literature in the field.

In particular one may cite perfuming co-ingredients which are commonly used in perfume formulations, such as:
Aldehydic ingredients: decanal, dodecanal, 2-methyl-undecanal, 10-undecenal, octanal and/or nonenal;
Aromatic-herbal ingredients: *eucalyptus* oil, camphor, eucalyptol, menthol and/or alpha-pinene;
Balsamic ingredients: coumarine, ethylvanillin and/or vanillin;
Citrus ingredients: dihydromyrcenol, citral, orange oil, linalyl acetate, citronellyl nitrile, orange terpenes, limonene, 1-P-menthen-8-yl acetate and/or 1,4(8)-P-menthadiene;
Floral ingredients: Methyl dihydrojasmonate, linalool, Citronellol, phenylethanol, 3-(4-tert-butylphenyl)-2-methylpropanal, hexylcinnamic aldehyde, benzyl acetate, benzyl salicylate, tetrahydro-2-isobutyl-4-methyl-4(2H)-pyranol, beta ionone, methyl 2-(methylamino)benzoate, (E)-3-methyl-4-(2,6,6-trimethyl-2-cyclohexen-1-yl)-3-buten-2-one, hexyl salicylate, 3,7-dimethyl-1,6-nonadien-3-ol, 3-(4-isopropylphenyl)-2-methylpropanal, verdyl acetate, geraniol, P-menth-1-en-8-ol, 4-(1,1-dimethylethyl)-1-cyclohexyle acetate, 1,1-dimethyl-2-phenylethyl acetate, 4-cyclohexyl-2-methyl-2-butanol, amyl salicylate, high cis methyl dihydrojasmonate, 3-methyl-5-phenyl-1-pentanol, verdyl proprionate, geranyl acetate, tetrahydro linalool, cis-7-P-menthanol, Propyl (S)-2-(1,1-dimethylpropoxy)propanoate, 2-methoxynaphthalene, 2,2,2-trichloro-1-phenylethyl acetate, 4/3-(4-hydroxy-4-methylpentyl)-3-cyclohexene-1-carbaldehyde,
amylcinnamic aldehyde, 4-phenyl-2-butanone, isononyle acetate, 4-(1,1-dimethylethyl)-1-cyclohexyl acetate, verdyl isobutyrate and/or mixture of methyl-ionones isomers;
Fruity ingredients: gamma undecalactone, 4-decanolide, ethyl 2-methyl-pentanoate, hexyl acetate, ethyl 2-methylbutanoate, gamma nonalactone, allyl heptanoate, 2-phenoxyethyl isobutyrate, ethyl 2-methyl-1,3-dioxolane-2-acetate and/or diethyl 1,4-cyclohexane dicarboxylate;
Green ingredients: 2,4-Dimethyl-3-cyclohexene-1-carbaldehyde, 2-tert-butyl-1-cyclohexyl acetate, styrallyl acetate, allyl (2-methylbutoxy)acetate, 4-methyl-3-decen-5-ol, diphenyl ether, (Z)-3-hexen-1-ol and/or 1-(5, 5-dimethyl-1-cyclohexen-1-yl)-4-penten-1-one;
Musk ingredients: 1,4-dioxa-5,17-cycloheptadecanedione, pentadecenolide, 3-Methyl-5-cyclopentadecen-1-one, 1,3,4,6,7,8-hexahydro-4,6,6,7,8,8-hexamethyl-cyclopenta-[G]isochromene, (1S,1'R)-2-[1-(3',3'-dimethyl-1'-cyclohexyl)ethoxy]-2-methylpropyl propanoate, and/or (1S,1'R)-[1-(3',3'-Dimethyl-1'-cyclohexyl)ethoxycarbonyl]methyl propanoate;
Woody ingredients: 1-(octahydro-2,3,8,8-tetramethyl-2-naphtalenyl)-1-ethanone, patchouli oil, terpenes fractions of patchouli oil, (1'R,E)-2-ethyl-4-(2',2',3'-trimethyl-3'-cyclopenten-1'-yl)-2-buten-1-ol, 2-ethyl-4-(2, 2,3-trimethyl-3-cyclopenten-1-yl)-2-buten-1-ol,
Methyl cedryl ketone, 5-(2,2,3-trimethyl-3-cyclopentenyl)-3-methylpentan-2-ol, 1-(2,3,8,8-tetramethyl-1,2,3, 4,6,7,8,8a-octahydronaphthalen-2-yl)ethan-1-one and/or isobornyl acetate;
Other ingredients (e.g. amber, powdery spicy or watery): dodecahydro-3a,6,6,9a-tetramethyl-naphtho[2,1-b]
furan and any of its stereoisomers, heliotropin, anisic aldehyde, eugenol, cinnamic aldehyde, clove oil, 3-(1,3-benzodioxol-5-yl)-2-methylpropanal and/or 3-(3-isopropyl-1-phenyl)butanal.

In particular, one may cite the following perfuming co-ingredients, having floral notes: Methyl dihydrojasmonate, linalool, 3-(4-tert-butylphenyl)-2-methylpropanal, hexylcinnamic aldehyde, tetrahydro-2-isobutyl-4-methyl-4(2H)-pyranol, 3,7-dimethyl-1,6-nonadien-3-ol, 3-(4-isopropylphenyl)-2-methylpropanal, 4-cyclohexyl-2-methyl-2-butanol, high cis methyl dihydrojasmonate, tetrahydro linalool.

A perfumery base according to the invention may not be limited to the above mentioned perfuming co-ingredients, and many other of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" it is meant here an ingredient capable of imparting additional added benefit such as a color, a particular light resistance, chemical stability, etc. A detailed description of the nature and type of adjuvant commonly used in perfuming composition cannot be exhaustive, but it has to be mentioned that said ingredients are well known to a person skilled in the art. One may cite as specific non-limiting examples the following: viscosity agents (e.g. surfactants, thickeners, gelling and/or rheology modifiers), stabilizing agents (e.g. preservatives, antioxidant, heat/light and or buffers or chelating agents, such as BHT), coloring agents (e.g. dyes and/or pigments), preservatives (e.g. antibacterial or antimicrobial or antifungi or anti irritant agents), abrasives, skin cooling agents, fixatives, insect repellants, ointments, vitamins and mixtures thereof.

It is understood that a person skilled in the art is perfectly able to design optimal formulations for the desired effect by admixing the above mentioned components of a perfuming composition, simply by applying the standard knowledge of the art as well as by trial and error methodologies.

An invention's composition consisting of at least one compound of formula (I) and at least one compound of formula (II) and at least one perfumery carrier consist of a particular embodiment of the invention as well as a perfuming composition comprising at least one compound of formula (I) and one compound of formula (II), at least one perfumery carrier, at least one perfumery base, and, optionally, at least one perfumery adjuvant.

According to a particular embodiment, the perfuming compositions mentioned above comprise more than one compound of formula (I) and more than one compound of formula (II) and enable the perfumer to prepare accords or perfumes possessing the odor tonality of various compounds of the invention, creating thus new building block for creation purposes.

For the sake of clarity, it is also understood that any mixture resulting directly from a chemical synthesis, e.g. a reaction medium without an adequate purification, in which the invention's composition of matter would be involved as a starting, intermediate or end-product could not be considered as a perfuming composition according to the invention as far as said mixture does not provide the inventive composition of matter in a suitable form for perfumery.

The invention's composition of matter can also be advantageously used in all the fields of modern perfumery, i.e. fine or functional perfumery, to positively impart or modify the odor of a consumer product into which said invention's composition of matter is added. Consequently, another object of the present invention consists of a perfumed consumer product comprising, as a perfuming ingredient, at least one composition of matter comprising compound of formula (I) and compound of formula (II), as defined above.

The invention's composition of matter can be added as such or as part of an invention's perfuming composition.

For the sake of clarity, "perfumed consumer product" is meant to designate a consumer product which delivers at least a pleasant perfuming effect to the surface or space to which it is applied (e.g. skin, hair, textile, or home surface). In other words, a perfumed consumer product according to the invention is a perfumed consumer product which comprises a functional formulation, as well as optionally additional benefit agents, corresponding to the desired consumer product and an olfactive effective amount of at least one invention's composition of matter. For the sake of clarity, said perfumed consumer product is a non-edible product.

The nature and type of the constituents of the perfumed consumer product do not warrant a more detailed description here, which in any case would not be exhaustive, the skilled person being able to select them on the basis of his general knowledge and according to the nature and the desired effect of said product.

Non-limiting examples of suitable perfumed consumer product include a perfume, such as a fine perfume, a splash or eau de parfum, a cologne or a shave or after-shave lotion; a fabric care product, such as a liquid or solid detergent, a fabric softener, a liquid or solid scent booster, a fabric refresher, an ironing water, a paper, a bleach, a carpet cleaner, a curtain-care product; a body-care product, such as a hair care product (e.g. a shampoo, a coloring preparation or a hair spray, a color care product, a hair shaping product, a dental care product), a disinfectant, an intimate care product; a cosmetic preparation (e.g. a skin cream or lotion, a vanishing cream or a deodorant or antiperspirant (e.g. a spray or roll on), a hair remover, a tanning or sun or after sun product, a nail product, a skin cleansing, a makeup); or a skin-care product (e.g. a soap, a shower or bath mousse, oil or gel, or a hygiene product or a foot/hand care products); an air care product, such as an air freshener or a "ready to use" powdered air freshener which can be used in the home space (rooms, refrigerators, cupboards, shoes or car) and/or in a public space (halls, hotels, malls, etc.); or a home care product, such as a mold remover, a furnisher care, a wipe, a dish detergent or a hard-surface (e.g. a floor, bath, sanitary or a windows) detergent; a leather care product; a car care product, such as a polish, a waxes or a plastic cleaner.

Some of the above-mentioned perfumed consumer products may represent an aggressive medium for the invention's composition of matter, so that it may be necessary to protect the latter from premature decomposition, for example by encapsulation or by chemically binding it to another chemical which is suitable to release the invention's composition of matter upon a suitable external stimulus, such as an enzyme, light, heat or a change of pH.

The proportions in which the composition of matter according to the invention can be incorporated into the various aforementioned products or perfuming compositions vary within a wide range of values. These values are dependent on the nature of the article to be perfumed and on the desired organoleptic effect as well as on the nature of the co-ingredients in a given base when the composition of matter according to the invention are mixed with perfuming co-ingredients, solvents or additives commonly used in the art.

For example, in the case of perfuming compositions, typical concentrations are in the order of 0.01%, or even of 1%, to 15%, or even 25%, by weight, or even more, of the composition of matter based on the weight of the composition into which they are incorporated. In the case of perfumed consumer product, typical concentrations are in the order of 0.01% to 1%, or even 2%, or even more, by weight of the invention's composition of matter based on the weight of the consumer product into which they are incorporated.

Concentrations lower than these, such as in the order of 0.01% to 1%, or even 2%, by weight, can be used when this composition of matter is incorporated into perfuming consumer products, percentage being relative to the weight of the article.

Another object of the present invention is a process for preparing a composition of matter comprising compound of formula (I) and compound of formula (II) as defined above. The process to prepare said composition comprises the step of reacting allyl alcohol or crotyl alcohol with compound of formula

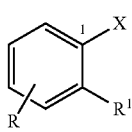
(V)

in the form of any one of its regioisomers or a mixture thereof; and
wherein $R^1$ and R have the same meaning as above; said R being, relative to position 1, an ortho, a meta, a para substituent of the aromatic ring or a mixture thereof; and X represents an iodide or a bromide atom or a diazo, a triflate or a tosylate group, preferably a bromide atom;
under Heck coupling conditions.

For the sake of clarity, allyl alcohol is meant to designate prop-2-en-1-ol and crotyl alcohol is meant to designate but-2-en-1-ol.

For the sake of clarity, by the expression "Heck coupling conditions", or the similar, it is meant the normal meaning understood by a person skilled in the art, i.e. the reaction is performed in a presence of palladium ($Pd^0$) catalyst and a base. The person skilled in the art will be able to set up the best conditions. The palladium catalyst comprises a phosphine ligand and may be generated in situ from palladium precatalyst and phosphines.

The palladium catalysts or precatalysts that can be used in the present invention include but are not limited to $Pd(dba)_2$, $Pd(OAc)_2$, $Pd[P(t-Bu_3)]_2$ or $Pd_2(dba)_3$. Preferably, the palladium complex is selected from the group consisting of $Pd(dba)_2$ and $Pd_2(dba)_3$.

The palladium catalyst or precatalyst can be added into the reaction medium of the invention's process in a large range of concentrations. As non-limiting examples, one can cite as complex concentration values those ranging from about 0.1 mol % to about 10 mol %, relative to the amount of substrate. Preferably, the complex concentration will be comprised between 1 mol % to 3 mol %, relative to the amount of substrate. It goes without saying that the optimum concentration of complex will depend, as the person skilled in the art knows, on the nature of the latter, on the nature of the substrate, on the nature of the base, on the reaction temperature as well as on the desired time of reaction.

The phosphines, that can be used in the present invention, may be monodentate. Preferably, the phosphines that can be used in the present invention may be electron rich and sterically hindered; e.g. said phosphine may comprise at least one tert-butyl or ortho-tolyl group. Even more preferably, the phosphines that can be used in the present invention include but are not limited to tri-tert-butylphosphine, 2-(di-tert-butylphosphanyl)-1-phenyl-1H-indole, 2-(di-tert-butylphosphanyl)-1-(2-methoxyphenyl)-1H-pyrrole, tri-ortho-tolylphosphine, tri(furan-2-yl)phosphane or $PPh_3$. Preferably, the phosphines are selected from the group consisting of tri-tert-butylphosphine, 2-(di-tert-butylphosphanyl)-1-phenyl-1H-indole and 2-(di-tert-butylphosphanyl)-1-(2-methoxyphenyl)-1H-pyrrole. The phosphine can be added into the reaction medium of the invention's process in a large range of concentrations. As non-limiting examples, one can cite as phosphine concentration values those ranging from about 0.2 mol % to about 30 mol %, relative to the amount of the of substrate. Preferably, the phosphine concentration will be comprised between 0.4 mol % to 10 mol %. The optimum concentration of the phosphine will depend, as the person skilled in the art knows, on the nature of the latter, on the nature of the substrate, on the nature of the base, on the reaction temperature as well as on the desired time of reaction.

The bases that can be used in the present invention include but are not limited to potassium or sodium acetate, potassium or sodium bicarbonate, potassium or sodium carbonate, secondary or tertiary amines such as triethyl amine or N-cyclohexyl-N-methylcyclohexanamine. Preferably the base may be N-cyclohexyl-N-methylcyclohexanamine. The amine can be added into the reaction medium of the invention's process in a large range of concentrations. As non-limiting examples, one can cite as base concentration values those ranging from about 1 molar equivalent to about 3 molar equivalent, relative to the amount of the substrate. Preferably, the base concentration will be comprised between 1 molar equivalent to 1.5 molar equivalent. The optimum concentration of the base will depend, as the person skilled in the art knows, on the nature of the latter, on the nature of the substrate, on the nature of the base, on the reaction temperature as well as on the desired time of reaction.

The allylic alcohol or crotyl alcohol can be added into the reaction medium of the invention's process in a large range of concentrations. As non-limiting examples, one can cite as alcohol concentration values those ranging from about 1 molar equivalent to about 3 molar equivalent, relative to the amount of substrate. Preferably, the alcohol concentration will be comprised between 1 molar equivalent to 1.5 molar equivalent. It goes without saying that the optimum concentration of complex will depend, as the person skilled in the art knows, on the nature of the latter, on the nature of the substrate, on the nature of the base, on the reaction temperature as well as on the desired time of reaction. Preferably allyl alcohol is used.

According to any one of the above embodiments, the R group of compound of formula (V) may be an ortho, a meta, a para substituent of the aromatic ring, relative to position 1; i.e. the compound of formula (V) may be of formula (V'), (V''), (V'''). Preferably, the compound of formula (V) is compound (V''').

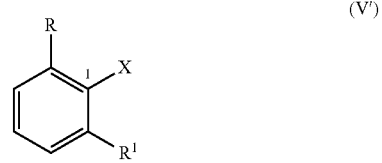
(V')

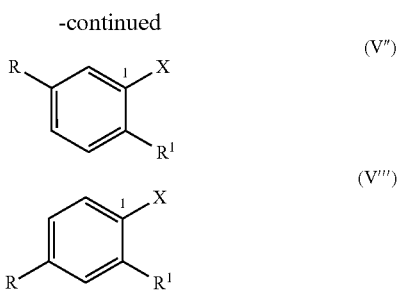

According to any one of the above embodiments, the compounds of formula (V) may be in a form of composition of matter comprising a mixture of regioisomers; i.e. a mixture comprising a compound wherein the R group is an ortho substituent relative to position 1 (compound of formula (V')), a compound wherein the R group is a meta substituent, relative to position 1 (compound of formula (V")) and a compound wherein the R group is an para substituent relative to position 1 (compound of formula (V''')).

Preferably said mixture comprises
at most 40 wt % of the compound of formula (V');
at most 10 wt % of the compound of formula (V"); and
at least 50 wt % of the compound of formula (V''').
Even more preferably, said mixture comprises
at most 15 wt % of the compound of formula (V');
at most 15 wt % of the compound of formula (V"); and
at least 70 wt % of the compound of formula (V''').
Even more preferably, said mixture comprises
at most 5 wt % of the compound of formula (V');
at most 5 wt % of the compound of formula (V"); and
at least 90 wt % of the compound of formula (V''').

According to a preferred embodiment, the R group of compound of formula (V) is a meta and/or a para substituent of the aromatic ring, relative to position 1; i.e. the compound of formula (V) may be of formula (V") and/or (V'''). Preferably, the R group of compound of formula (V) is a para substituent of the aromatic ring, relative to position 1; i.e. the compound of formula (V) is of formula (V''').

According to any one of the above embodiments, the compound of formula (V) can be prepared according to methods reported in the literature or standard methods known in the art; for example, by the functionalization of a benzene derivative of formula (VI)

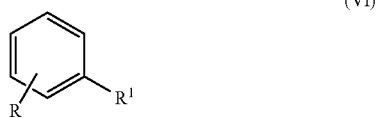

in the form of any one of its regioisomers or a mixture thereof; and
wherein $R^1$ and R have the same meaning as above.

According to a particular embodiment of the invention, the compound of formula (V) can be prepared by the bromation of 2-methyl-1-phenylpropan-2-ol or 2-methyl-4-phenylbutan-2-ol which are commercially available. Said method provides different regioisomers which could be purified or use as a mixture.

According to another particular embodiment of the invention, the compound of formula (V) can be prepared by the addition of a Methyl Grignard on an alkyl (bromophenyl) acetate.

According to a particular embodiment, the process to prepare the invention's composition of matter comprises the step of reacting methyl or ethyl acrylate instead of allylic alcohol with compound of formula (V) under Heck coupling conditions. In order to obtain the invention's composition of matter, the compounds obtained via said Heck coupling have to be reduced under conditions known by the person skilled in the art.

According to any one of the above embodiments, the compound of formula (V) is a compound of formula

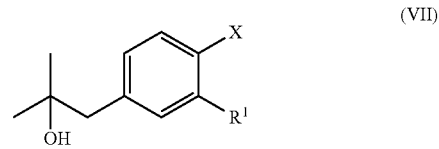

wherein $R^1$ has the same meaning as defined above.

The Heck coupling reaction can be carried out in the presence of a solvent. Any solvent current in such reaction type can be used for the purposes of the invention. Non-limiting examples include dioxane, dimethyl sulfoxide, acetonitrile, $C_{6-12}$ aromatic solvents such as toluene, 1,3-diisopropylbenzene, cumene or pseudocumene, amide such N,N-dimethylformamide or N-methylformamide, or mixtures thereof. The choice of the solvent is a function of the nature of the substrate and/or catalyst and the person skilled in the art is well able to select the solvent most suitable in each case to optimize the reaction.

The Heck coupling step can be carried out at a temperature in the range comprised between 20° C. and 120° C., more preferably in the range of between 80° C. and 110° C., or even between 90° C. and 100° C. Of course, a person skilled in the art is also able to select the preferred temperature according to the melting and boiling point of the starting and final products as well as the desired time of reaction or conversion.

It is understood that the composition of matter, may comprise various regioisomers, such as the ortho, para or meta products depending on the purity of the staring materials.

EXAMPLES

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) with a 400 or 500 MHz machine for $^1H$ and $^{13}C$, the chemical shifts δ are indicated in ppm with respect to TMS as standard, the coupling constants J are expressed in Hz.

Example 1

Preparation of invention's composition comprising 2-(4-(2-hydroxy-2-methylpropyl)phenyl)propanal (compound of formula (I)) and 3-(4-(2-Hydroxy-2-methylpropyl)phenyl)propanal (compound of formula (II))

a) Preparation of 1-(4-Bromophenyl)-2-methylpropan-2-ol

A 200 ml round bottomed flask were charged methylmagnesium bromide (19 g, 3M in methyltetrahydrofuran, 57 mmol) and 2-methyltetrahydrofuran (25 g). This solution was stirred at 0° C. A solution of ethyl 2-(4-bromophenyl)acetate (5 g, 20.6 mmol) in 2-methyltetrahydrofuran (15 g) was added over a period of 30 minutes. The reaction mixture was then stirred further for 3 hours. The reaction mixture was quenched with acetic acid (30 g, 20% aqueous solution) and phases were separated. The organic phase was washed with water, 5% $Na_2CO_3$ solution, water and evaporated down to yield crude 1-(4-bromophenyl)-2-methylpropan-2-ol (4.4 g) which was purified by distillation (3.85 g, 82% yield).

$^1$H NMR (500 MHz, $CDCl_3$): δ=1.20 (s, 6H), 1.45 (br, 1H), 2.70 (s, 2H), 7.10-7.06 (m, 2H), 7.44-7.40 (m, 2H) ppm.

$^{13}$C NMR (125 MHz, $CDCl_3$): δ=136.8 (s), 132.1 (d), 131.2 (d), 120.5 (s), 70.6 (s), 49.1 (t), 29.2 (q) ppm.

b) Preparation of a 1-(4-Bromophenyl)-2-methylpropan-2-ol and 1-(2-Bromophenyl)-2-methylpropan-2-ol To a solution of 2-methyl-1-phenylpropan-2-ol (91.5 g, 609 mmol, 1 equiv.) and iron (III) chloride (9.88 g, 60.9 mmol, 0.1 equiv.) in acetonitrile (305 mL) was added 1,3-dibromo-5,5-dimethylhydantoin (96 g, 335 mmol, 0.55 equiv.) portionwise. After stirring at r.t. for 3 days, the reaction was quenched with water. It was extracted twice with ether, the combined organic extracts were washed with a 10% sodium thiosulfate solution, dried over sodium sulfate and the solvents were evaporated. The residue was purified by bulb-to-bulb distillation (0.07 mbar, 75° C.) and distillation on a Fischer column to afford pure 1-(4-bromophenyl)-2-methylpropan-2-ol (57.1 g, 41% yield) and pure 1-(2-bromophenyl)-2-methylpropan-2-ol (34.2 g, 25% yield).

1-(4-bromophenyl)-2-methylpropan-2-ol $^1$H NMR (500 MHz, $CDCl_3$): δ=1.21 (s, 6H), 2.71 (s, 2H), 7.09 (d, J=8.3 Hz, 2H), 7.43 (d, J=8.3 Hz, 2H).

$^{13}$C NMR (125 MHz, $CDCl_3$): δ=136.8 (s), 132.2 (d, 2C), 131.2 (d, 2C), 120.5 (s), 70.7 (s), 49.1 (t), 29.2 (q, 2C).

1-(2-bromophenyl)-2-methylpropan-2-ol $^1$H NMR (500 MHz, $CDCl_3$): δ=1.28 (s, 6H), 3.01 (s, 2H), 7.08 (m, 1H), 7.25 (m, 1H), 7.35 (dd, J=7.7, 1.7 Hz, 1H), 7.57 (dd, J=8.0, 1.2 Hz, 1H).

13C NMR (125 MHz, $CDCl_3$): δ=137.7 (s), 133.1 (d), 132.3 (d), 128.1 (d), 127.1 (d), 126.0 (s), 71.8 (s), 48.0 (t), 29.5 (q, 2C).

c) Preparation of a composition comprising 2-(4-(2-hydroxy-2-methylpropyl)phenyl)propanal and 3-(4-(2-hydroxy-2-methylpropyl)phenyl)propanal In a 100 ml round bottomed flask were charged under an argon atmosphere 1-(4-Bromophenyl)-2-methylpropan-2-ol (5 g, 21.7 mmol), N,N-dimethyl formamide (10 g), N-cyclohexyl-N-methylcyclohexanamine (4.8 g, 23.8 mmol) and allyl alcohol (1.38 g, 23.8 mmol); this solution was degassed for one hour. 2-(di-tert-butylphosphino)-1-phenyl-1H-indole (0.093 g, 0.26 mmol) and bis(dibenzylideneacetone) palladium (0) (0.052 g, 0.09 mmol) were added and the reaction mixture was heated at 100° C. for 1 hour, then cooled to room temperature. The mixture was diluted with toluene and washed with water, 10% aqueous HCl, 5% $NaHCO_3$ solution and water. Organic phase was concentrated to furnish crude (3.9 g) which was purified by distillation (3.05 g, 68% yield, containing 15% of 2-(4-(2-hydroxy-2-methylpropyl)phenyl)propanal and 85% of 3-(4-(2-hydroxy-2-methylpropyl)phenyl)propanal).

3-(4-(2-hydroxy-2-methylpropyl)phenyl)propanal $^1$H NMR (500 MHz, $CDCl_3$): δ=1.21 (s, 6H), 1.64-1.56 (br, 1H), 2.72 (s, 2H), 2.79-2.74 (m, 1H), 2.93 (t, 2H), 7.16-7.1 (m, 4H), 9.8 (t, 1H) ppm.

$^{13}$C NMR (125 MHz, $CDCl_3$): δ=201.7 (s), 138.4 (s), 135.8 (s), 130.7 (d), 128.1 (d), 70.7 (s), 49.3 (t), 45.2 (t), 29.2 (q), 27.7 (t) ppm.

2-(4-(2-hydroxy-2-methylpropyl)phenyl)propanal $^1$H NMR (500 MHz, $CDCl_3$): δ=1.23 (s, 6H), 1.44 (d, J=7.0 Hz, 3H), 2.76 (s, 2H), 3.62 (dd, J=7.0, 1.4 Hz, 1H), 7.15 (d, J=8.1 Hz, 2H), 7.24 (d, J=8.1 Hz, 2H), 9.67 (d, J=1.4 Hz, 1H).

$^{13}$C NMR (125 MHz, $CDCl_3$): δ=201.1 (d), 137.2 (s), 135.8 (s), 131.2 (d, 2C), 128.1 (d, 2C), 70.8 (s), 52.6 (d), 49.3 (t), 29.2 (q, 2C), 14.6 (q).

Example 2

Preparation of invention's composition comprising 2-(4-(2-hydroxy-2-methylpropyl)phenyl)propanal (compound of formula (I)) and 3-(4-(2-hydroxy-2-methylpropyl)phenyl)propanal (compound of formula (II)) using different phosphines The same procedure reported in example 1 c) has been reproduced by replacing 2-(di-tert-butylphosphino)-1-phenyl-1H-indole by the same amount in mmol of phophines reported in Table 1.

TABLE 1

| Phosphine used in Heck reaction conditions | | | | |
|---|---|---|---|---|
| Phosphine | % Conv. 1 h | % Conv. 2.5 h | % Conv. 6 h | l/b ratio |
| 2-(di-tert-butylphosphino)-1-phenyl-1H-indole | 99.1 | 99.6 | 100 | 85/15 |
| $P(tBu)_3HBF_4$ | 95 | 98.4 | 100 | 85/15 |
| $P(o-Tolyl)_3$ | 90 | 90 | 90 | 85/15 |
| $P(Phenyl)_3$ | 10 | 24 | 26 | 82/18 |

Example 3

Preparation of invention's composition comprising 2-(3-(2-hydroxy-2-methylpropyl)phenyl)butanal (compound of formula (I)) and 3-(3-(2-hydroxy-2-methylpropyl)phenyl)butanal (compound of formula (II))

a) Preparation of 1-(3-bromophenyl)-2-methylpropan-2-ol

To a solution of 1,3-dibromobenzene (27.1 g, 115 mmol, 1 equiv.) in THF (383 mL) at −78° C. was added n-BuLi (1.6 M, 79 mL, 127 mmol, 1.1 equiv.) dropwise. After stirring at −78° C. for 1.5 hour, the temperature was allowed to reach −50° C. and isobutylene oxide (12.3 mL, 138 mmol, 1.2 equiv.) was added dropwise. After stirring at −50° C. for 30 min, boron trifluoride etherate (19.0 mL, 150 mmol, 1.3 equiv.) was added dropwise. After stirring at −50° C. for 1.5 hour, the reaction was quenched with a 10% w/w solution of Na/K tartrates and the mixture was allowed to reach room temperature overnight. It was extracted three times with ether, the combined organic extracts were dried over sodium sulfate and the solvent was evaporated. The residue was purified by bulb-to-bulb distillation (125-130° C., 0.24-0.30 mbar) to afford 1-(3-bromophenyl)-2-methylpropan-2-ol as an oil (16.3 g, 91% purity, 57% yield).

$^1$H NMR (500 MHz, CDCl$_3$): δ=1.23 (s, 6H), 2.73 (s, 2H), 7.13-7.19 (m, 2H), 7.37-7.39 (m, 2H).

$^{13}$C NMR (125 MHz, CDCl$_3$): δ=140.2 (s), 133.4 (d), 129.7 (d), 129.6 (d), 129.1 (d), 122.2 (s), 70.8 (s), 49.3 (t), 29.2 (q, 2C).

b) Preparation of a composition comprising 2-(3-(2-hydroxy-2-methylpropyl)phenyl)butanal (compound of formula (I)) and 3-(3-(2-hydroxy-2-methylpropyl)phenyl)butanal (compound of formula (II))

A solution of 1-(3-bromophenyl)-2-methylpropan-2-ol (5.00 g, 18.8 mmol, 1 equiv.) and N-cyclohexyl-N-methyl-aminecyclohexanamine (4.73 mL, 20.6 mmol, 1.1 equiv.) in DMF (37.5 mL) was degassed and stirred under an argon atmosphere for 20 min. Crotyl alcohol (1.76 mL, 20.6 mmol, 1.1 equiv.) and bis(dibenzylideneacetone)palladium(0) (108 mg, 0.19 mmol, 0.01 equiv.) were added, followed by 2-(tert-butylphosphino)-1-phenyl-1H-indole (190 mg, 0.56 mmol, 0.03 equiv.) and the reaction was heated to 100° C. for 45 min. After cooling down to r.t., it was diluted with ether and washed three times with water. The organic layer was dried over sodium sulfate and the solvent was evaporated. The residue (GC ratio of linear/branched products: 2.5:1) was purified by flash column chromatography on silica gel (Heptane/AcOEt 7:3) and bulb-to-bulb distillation (130-140° C., 0.15 mbar) to afford the desired 3-(3-(2-hydroxy-2-methylpropyl)phenyl)butanal (1.62 g, 39% yield) and 2-(3-(2-hydroxy-2-methylpropyl)phenyl)butanal (586 mg, 14%).

3-(3-(2-hydroxy-2-methylpropyl)phenyl)butanal $^1$H NMR (500 MHz, CDCl$_3$): δ=1.22 (s, 6H), 1.32 (d, J=7.0 Hz, 3H), 2.63-2.78 (m, 2H), 2.75 (s, 2H), 3.35 (sext, J=7.1 Hz, 1H), 7.06-7.12 (m, 3H), 7.25 (m, 1H), 9.70 (t, J=2.0 Hz, 1H).

$^{13}$C NMR (125 MHz, CDCl$_3$): δ=201.8 (d), 145.3 (s), 138.2 (s), 129.1 (d), 128.7 (d), 128.5 (d), 124.8 (d), 70.7 (s), 51.8 (t), 49.7 (t), 34.2 (d), 29.2 (q, 2C), 22.2 (q).

2-(3-(2-hydroxy-2-methylpropyl)phenyl)butanal $^1$H NMR (500 MHz, CDCl$_3$): δ=0.90 (t, J=7.4 Hz, 3H), 1.22 (s, 6H), 1.76 (m, 1H), 2.11 (m, 1H), 2.77 (s, 2H), 3.40 (m, 1H), 7.04 (s, 1H), 7.08 (d, J=7.6 Hz, 1H), 7.16 (d, J=7.6 Hz, 1H), 7.31 (t, J=7.6 Hz, 1H), 9.67 (d, J=2.0 Hz, 1H).

$^{13}$C NMR (125 MHz, CDCl$_3$): δ=201.0 (d), 138.7 (s), 136.2 (s), 131.0 (d), 129.6 (d), 128.8 (d), 126.9 (d), 70.7 (s), 60.7 (d), 49.6 (t), 29.2 (q, 2C), 23.0 (t), 11.7 (q).

What is claimed is:

1. A composition of matter comprising:
   a) at least one compound of formula

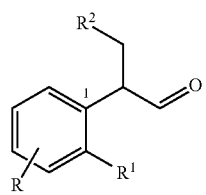

(I)

in the form of any one of its isomers or a mixture thereof; wherein $R^1$ represents a hydrogen atom or a $C_{1-2}$ alkyl group; $R^2$ represents a hydrogen atom or a methyl group; and R represents a group of formula $[CH_2]_nC(Me)_2OH$, wherein n is 1 or 2; said R being, relative to position 1, an ortho, a meta, a para substituent of the aromatic ring or a mixture thereof; and b) at least one compound of formula

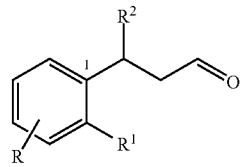

(II)

in the form of any one of its isomers or a mixture thereof; wherein $R^1$, $R^2$ and R have the same meaning as defined in formula (I); said R being, relative to position 1, an ortho, a meta, a para substituent of the aromatic ring or a mixture thereof.

2. The composition according to claim 1; wherein the compound of formula (I) is of formula

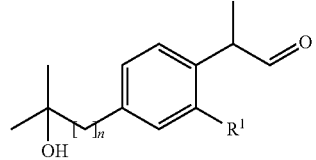

(III)

in the form of any one of its stereoisomers or a mixture thereof, and wherein n and $R^1$ have the same meaning as defined in claim 1.

3. The composition according to claim 1; wherein the compound of formula (II) is of formula

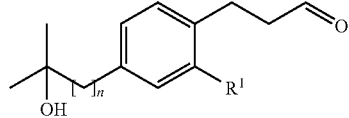

(IV)

wherein n and $R^1$ have the same meaning as defined in claim 1.

4. The composition according to claim 1, wherein $R^1$ is a hydrogen atom.

5. The composition according to claim 1, wherein n is 1.

6. The composition according to claim 1, wherein the composition comprises 2-(4-(2-hydroxy-2-methylpropyl)phenyl)propanal and 3-(4-(2-hydroxy-2-methylpropyl)phenyl)propanal.

7. The composition according to claim 6; wherein the composition comprises 3-[4-(2-hydroxy-2-methylpropyl)phenyl]propanal in an amount comprised between 50% w/w and 99% w/w and 2-[4-(2-hydroxy-2-methylpropyl)phenyl]propanal in an amount comprised between 0.5% w/w and 49% w/w, relative to the weight of the composition of matter.

8. A perfuming composition comprising
i) at least a composition of matter as defined in claim 1;
ii) at least one ingredient selected from the group consisting of a perfumery carrier and a perfumery base; and
iii) optionally at least one perfumery adjuvant.

9. A perfuming consumer product comprising at least a composition of matter as defined in claim 1.

10. The perfuming consumer product according to claim 9, wherein the perfumery consumer product is a perfume, a fabric care product, a body-care product, a cosmetic preparation, a skin-care product, an air care product or a home care product.

11. A perfuming consumer product according to claim 10, wherein the perfumery consumer product is a fine perfume, a splash or eau de perfume, a cologne, an shave or after-shave lotion, a liquid or solid detergent, a fabric softener, a fabric refresher, an ironing water, a paper, a bleach, a carpet cleaners, curtain-care products a shampoo, a coloring preparation, a color care product, a hair shaping product, a dental care product, a disinfectant, an intimate care product, a hair spray, a vanishing cream, a deodorant or antiperspirant, hair remover, tanning or sun product, nail products, skin cleansing, a makeup, a perfumed soap, shower or bath mousse, oil or gel, or a foot/hand care products, a hygiene product, an air freshener, a "ready to use" powdered air freshener, a mold remover, furnisher care, wipe, a dish detergent or hard-surface detergent, a leather care product, a car care product.

12. A process to prepare the composition of matter as defined in claim 1 comprising the step of reacting allyl alcohol or crotyl alcohol with compound of formula

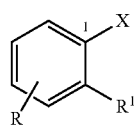

(V)

wherein $R^1$ and R have the same meaning in any one of claims 1 to 7; said R being, relative to position 1, an ortho, a meta, a para substituent of the aromatic ring or a mixture thereof; and X represents an iodide or a bromide atom or a diazo, a triflate or a tosylate group; under Heck coupling conditions.

13. The process according to claim 12, wherein process is performed in a presence of palladium ($Pd^0$) catalyst and a base.

14. A method to confer, enhance, improve or modify the odor properties of a perfuming composition or of a perfumed article, which method comprises adding to said composition or article an effective amount of at least a composition of matter as defined in claim 1.

15. A perfuming consumer product comprising a perfuming composition comprising
i) at least a composition of matter as defined in claim 1;
ii) at least one ingredient selected from the group consisting of a perfumery carrier and a perfumery base; and
iii) optionally at least one perfumery adjuvant.

16. The perfuming consumer product according to claim 9, wherein the perfumery consumer product is a perfume, a fabric care product, a body-care product, a cosmetic preparation, a skin-care product, an air care product or a home care product.

17. The perfuming consumer product according to claim 16, wherein the perfumery consumer product is a fine perfume, a splash or eau de perfume, a cologne, an shave or after-shave lotion, a liquid or solid detergent, a fabric softener, a fabric refresher, an ironing water, a paper, a bleach, a carpet cleaners, curtain-care products a shampoo, a coloring preparation, a color care product, a hair shaping product, a dental care product, a disinfectant, an intimate care product, a hair spray, a vanishing cream, a deodorant or antiperspirant, hair remover, tanning or sun product, nail products, skin cleansing, a makeup, a perfumed soap, shower or bath mousse, oil or gel, or a foot/hand care products, a hygiene product, an air freshener, a "ready to use" powdered air freshener, a mold remover, furnisher care, wipe, a dish detergent or hard-surface detergent, a leather care product, a car care product.

\* \* \* \* \*